(12) United States Patent
Worley et al.

(10) Patent No.: US 8,473,023 B2
(45) Date of Patent: *Jun. 25, 2013

(54) CATHETER WITH FLEXIBLE PRE-SHAPED TIP SECTION

(75) Inventors: Seth J. Worley, Lancaster, PA (US); Shiva Sharareh, Laguna Niguel, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 161 days.
This patent is subject to a terminal disclaimer.

(21) Appl. No.: 12/625,470

(22) Filed: Nov. 24, 2009

(65) Prior Publication Data
US 2010/0069734 A1 Mar. 18, 2010

Related U.S. Application Data

(63) Continuation of application No. 11/228,633, filed on Sep. 16, 2005, now Pat. No. 7,623,899.

(51) Int. Cl.
*A61B 5/04* (2006.01)
*A61B 18/14* (2006.01)

(52) U.S. Cl.
USPC .............................. 600/374; 606/41

(58) Field of Classification Search
USPC .............................. 600/374; 606/41
See application file for complete search history.

(56) References Cited

U.S. PATENT DOCUMENTS

| | | |
|---|---|---|
| 5,341,807 A | 8/1994 | Nardella |
| 5,617,854 A | 4/1997 | Munsif |
| 5,642,736 A | 7/1997 | Avitall |
| 5,643,197 A | 7/1997 | Brucker et al. |

(Continued)

FOREIGN PATENT DOCUMENTS
EP 0 839 547 A1 5/1998

OTHER PUBLICATIONS

Avitall, Boaz et al., New RF J Shaped Catheter Design for Creation of Circumferential Linear Lesions and PVS Isolation, Hearth Rhythm, p. S154, May Supplement 2005, vol. 2, No. 5.

(Continued)

*Primary Examiner* — Lee S Cohen
(74) *Attorney, Agent, or Firm* — Christie, Parker & Hale, LLP

(57) ABSTRACT

A catheter for mapping and/or ablating continuous linear or circumferential lesions at the intersection of a generally flat structure, such as the left atrium, and the ostium of generally cavernous regions of the heart, including pulmonary vein and the pulmonary venous antrum, comprises a catheter body with an intermediate section that is connected to a tip assembly by a highly flexible section. The intermediate section has at its distal end a preformed section, e.g., a curve, the intermediate section being deflectable in a direction opposite to the curve. The highly flexible section presets the tip assembly at an off-axis and/or off-plane angles from the preformed section. Accordingly, the preformed section is adapted to sit in the region and the preset angles of the ablation assembly enable contact with surrounding tissue. A high bending modulus enables the flexible section absorb displacement force applied to the ablation assembly, such as when the tip assembly encounters uneven tissue surface, without displacing the curve from the region. The tip assembly can be irrigated as enabled by a plurality of irrigation ports, a coil electrode, and a porous covering to disperse fluid over the outer surface of the tip assembly.

20 Claims, 16 Drawing Sheets

U.S. PATENT DOCUMENTS

| | | | |
|---|---|---|---|
| 5,823,955 | A | 10/1998 | Kuck et al. |
| 5,843,076 | A | 12/1998 | Webster, Jr. et al. |
| 5,916,214 | A | 6/1999 | Cosio et al. |
| 5,957,911 | A | 9/1999 | Nesto |
| 6,002,955 | A | 12/1999 | Willems et al. |
| 6,064,902 | A | 5/2000 | Haissaguerre et al. |
| 6,217,528 | B1 | 4/2001 | Koblish et al. |
| 6,224,587 | B1 | 5/2001 | Gibson |
| 6,319,250 | B1 | 11/2001 | Falwell et al. |
| 6,332,881 | B1 | 12/2001 | Carner et al. |
| 6,477,396 | B1 | 11/2002 | Mest et al. |
| 6,514,249 | B1 | 2/2003 | Maguire et al. |
| 6,572,611 | B1 | 6/2003 | Falwell |
| 6,582,429 | B2 | 6/2003 | Krishnan et al. |
| 6,623,449 | B2 | 9/2003 | Paskar |
| 6,638,278 | B2 | 10/2003 | Falwell et al. |
| 6,702,811 | B2 | 3/2004 | Stewart et al. |
| 7,623,899 | B2 * | 11/2009 | Worley et al. ............. 600/374 |
| 2002/0165441 | A1 | 11/2002 | Coleman et al. |
| 2003/0014044 | A1 | 1/2003 | Krishnan et al. |
| 2004/0015052 | A1 | 1/2004 | Barthel |
| 2004/0082948 | A1 | 4/2004 | Stewart et al. |
| 2004/0143175 | A1 | 7/2004 | Coleman et al. |
| 2004/0147827 | A1 | 7/2004 | Bowe |
| 2004/0181138 | A1 | 9/2004 | Hindricks et al. |
| 2005/0015082 | A1 | 1/2005 | O'Sullivan et al. |
| 2005/0187455 | A1 * | 8/2005 | Rashidi ............. 600/374 |
| 2006/0095030 | A1 | 5/2006 | Avitall et al. |
| 2006/0253116 | A1 | 11/2006 | Avitall et al. |

OTHER PUBLICATIONS

International Search Report mailed Feb. 2, 2007 for corresponding International Application No. PCT/US2006/036146, 4 sheets, indicating relevance of listed references in this IDS.

* cited by examiner

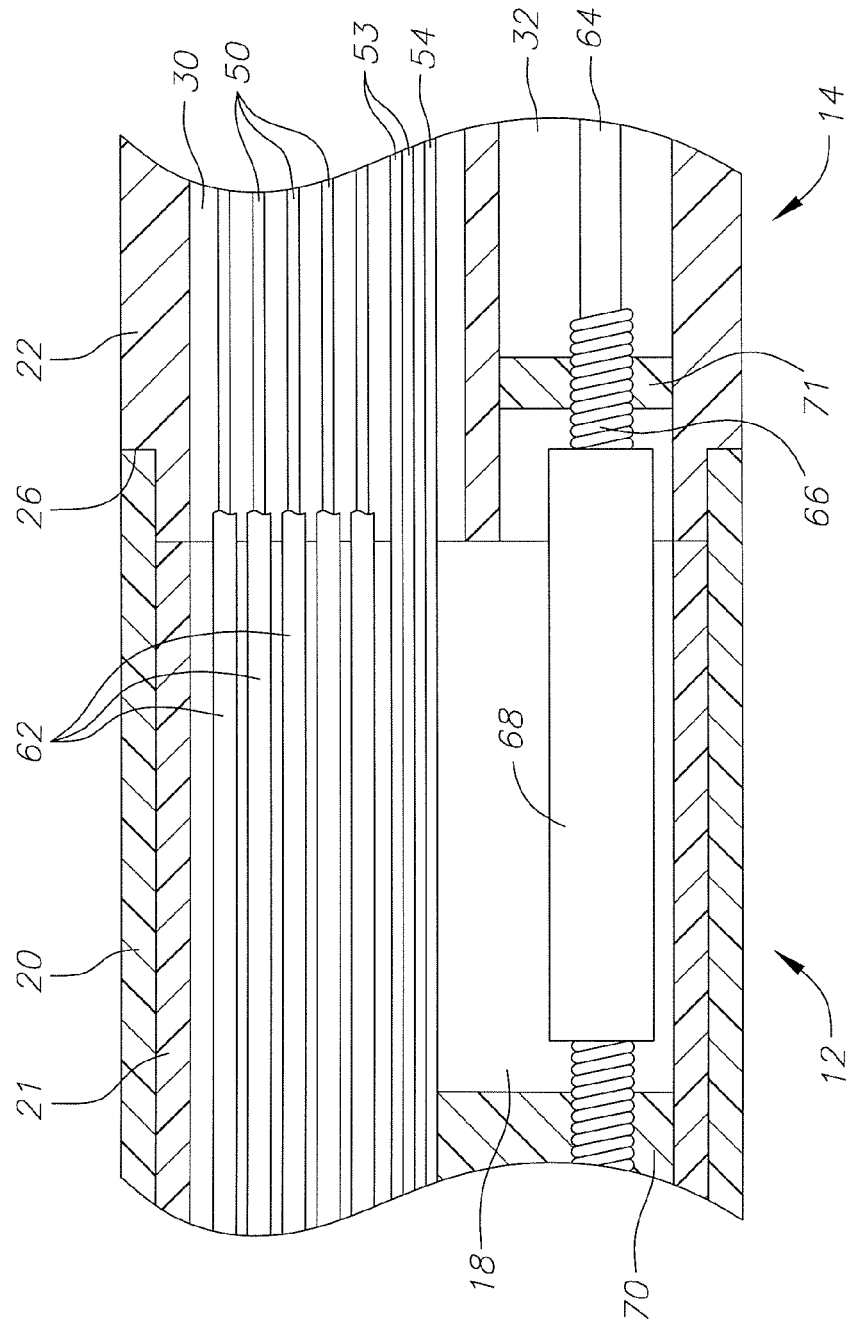

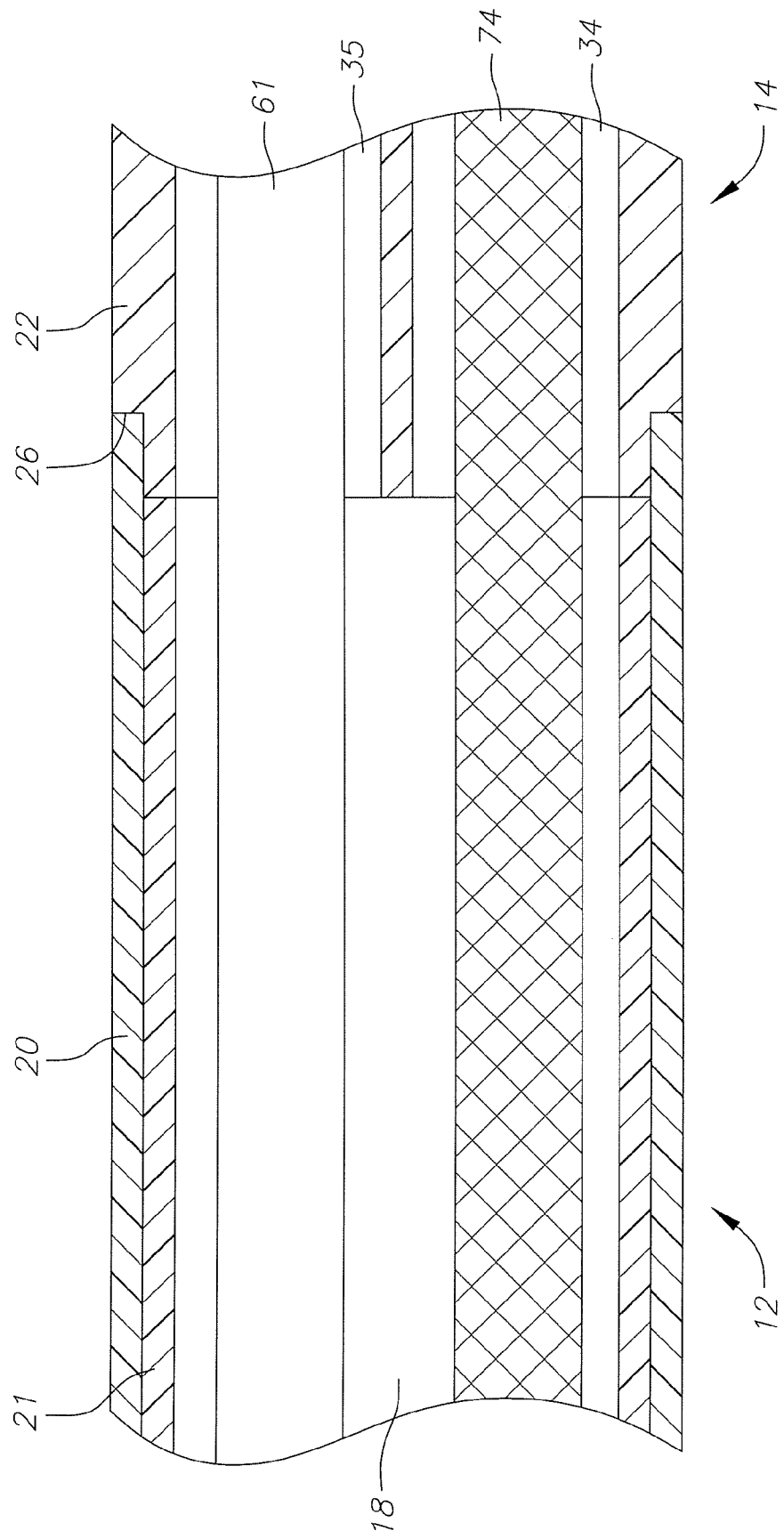

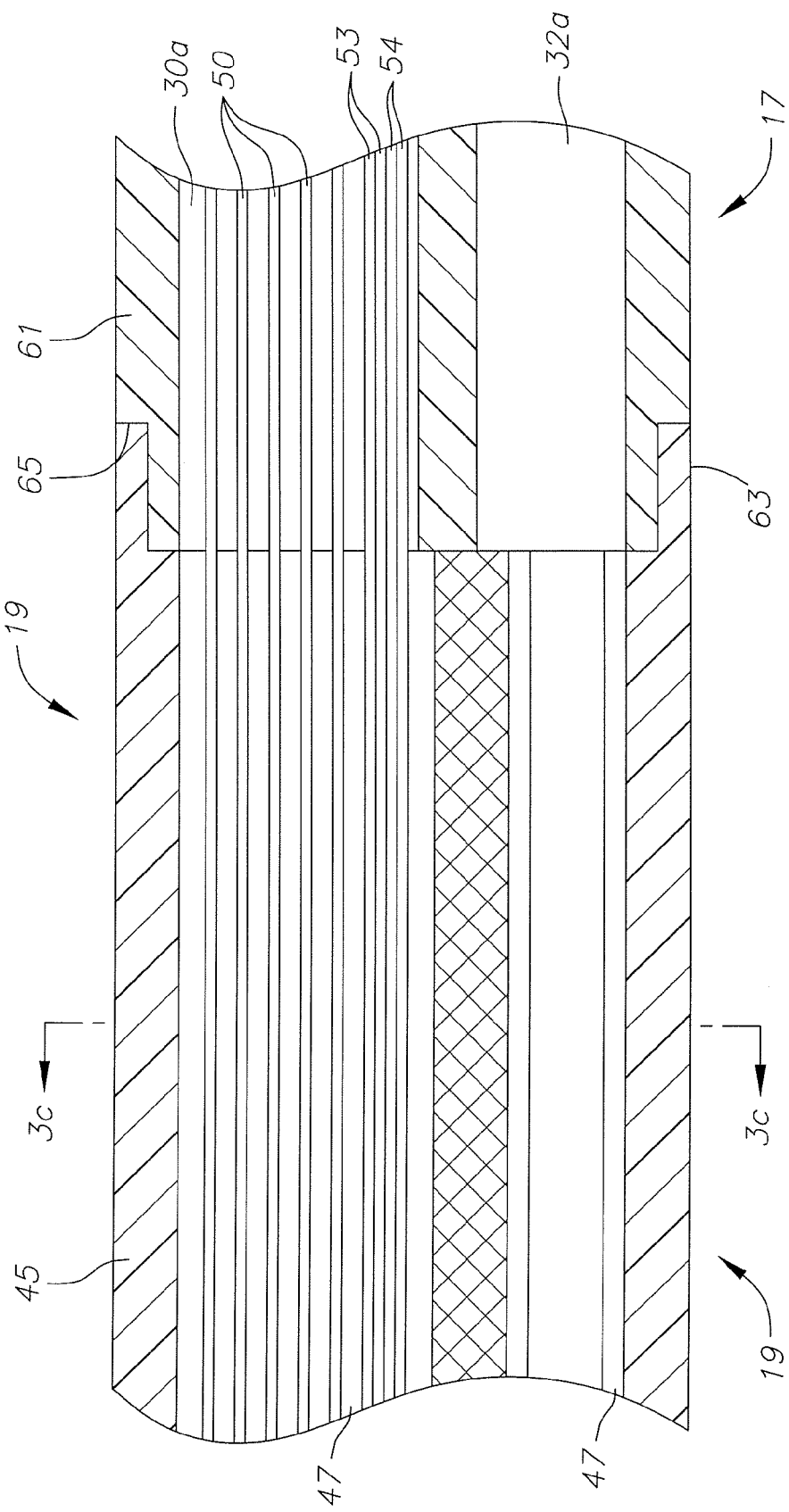

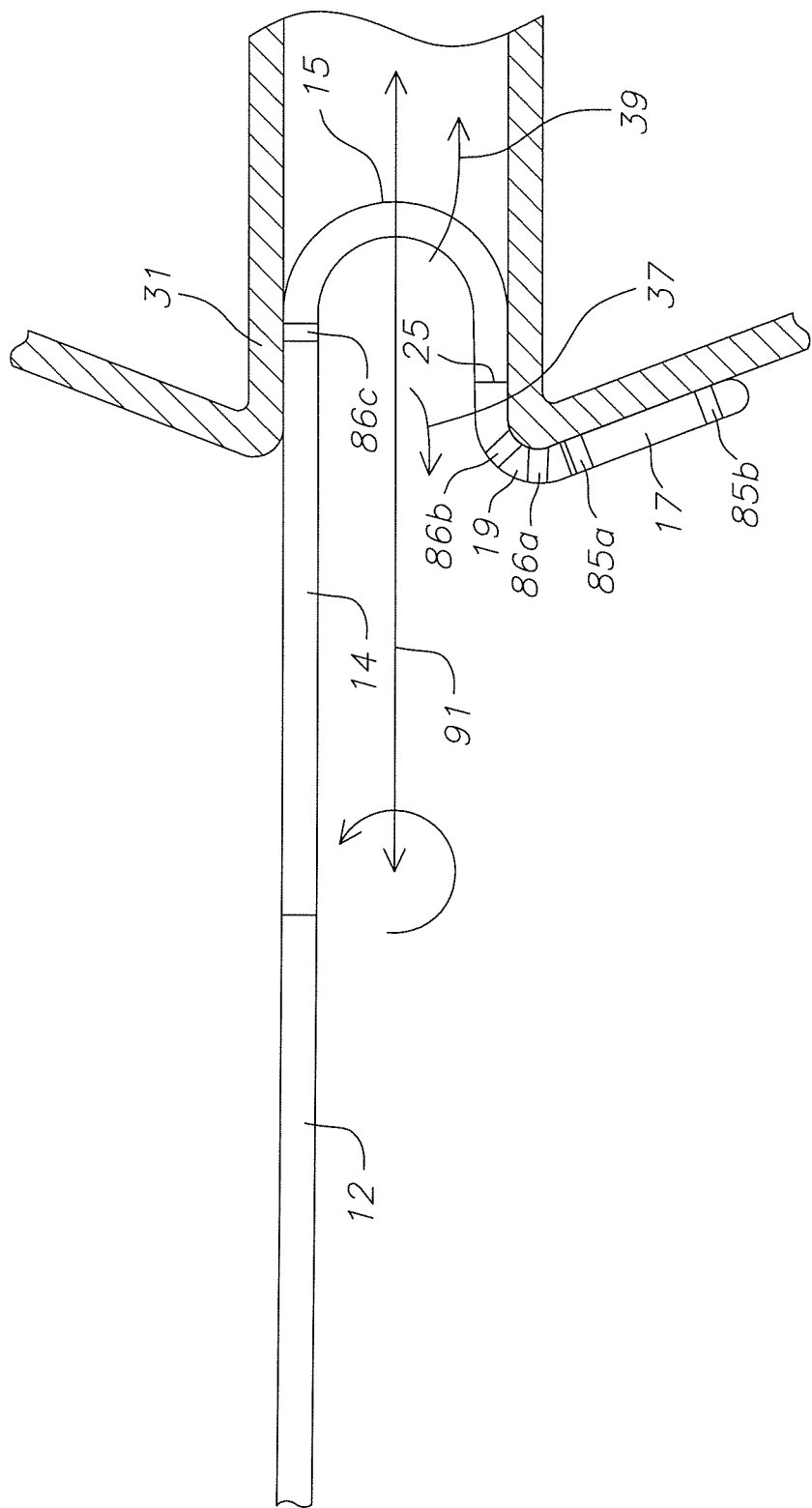

CATHETER WITH FLEXIBLE PRE-SHAPED TIP SECTION

CROSS-REFERENCE TO RELATED APPLICATION

This application is a continuation of U.S. patent application Ser. No. 11/228,633, filed Sep. 16, 2005, now U.S. Pat. No. 7,623,899, entitled "Catheter with Flexible Pre-Shaped Tip Section."

FIELD OF THE INVENTION

The invention is directed to a catheter having a tip assembly for mapping and/or ablating regions of or near a heart, including an intersection between a generally flat region such as the body of the left atrium and a generally cavernous regions such as a pulmonary vein or the antrum of two or more pulmonary veins, the intersection being referred to as the ostium or opening of the generally cavernous region.

BACKGROUND OF THE INVENTION

Atrial fibrillation is a common sustained cardiac arrhythmia and a major cause of stroke. This condition is initiated by wavelets originating at or near the intersection of a generally cavernous region such as a pulmonary venous atrium or a pulmonary vein and a generally flat structure such as the left atrium. The condition is perpetuated by reentrant wavelets propagating in an abnormal atrial-tissue substrate. Various approaches have been developed to interrupt wavelets, including surgical or catheter-mediated atriotomy. A common procedure involves ablating a lesion to interrupt the wavelets using one or more electrodes mounted on the distal end of a generally-straight catheter. This procedure works well, for example, when ablating a line of block in the atria. In this case, the proximal portion and tip of the catheter are in contact with and supported/stabilized by the atria along the line of intended block. However, at the intersection of a generally cavernous or tubular region and a generally flat region in or around the heart, this procedure can be less effective. For example, when the line of block to be ablated is about the circumference of the cavernous or tubular region, the catheter is not stabilized or supported except at the tip where it contacts the heart making it difficult to manipulate and control the distal end of a straight catheter for an effective ablation about the circumference. Catheters have been developed for ablating about an inner circumference of the tubular region, for example the pulmonary vein. For example, catheters using ultrasound transducers surrounded by an inflatable balloon have been used. The balloon in such a catheter is positioned inside the pulmonary vein. Balloons have also been used for stable placement inside the pulmonary vein, while ablating outside the pulmonary vein. However, due to the shape and material of the balloon, the balloon often becomes dislodged, thereby adversely affecting the accuracy of the lesion created outside the ostium of the pulmonary vein or pulmonary venous antrum. Moreover, due to the shape of regions near the pulmonary vein and/or the antrum of pulmonary veins, where a generally flat structure joins a generally cavernous structure, it is difficult to maintain a catheter in stable position. When the tip of the catheter approaches the intersection of a generally cavernous structure from the region of the generally flat structure the catheter section proximal the tip is not in contact with or supported/stabilized by the flat structure. Without supportive contact between this proximal catheter section and the tissue, motion of the heart during systole, diastole and respiration is not transmitted to this catheter section except by contact between tissue and the catheter tip. As the heart moves during systole, diastole and respiration, the contact pressure at the tip of the catheter may vary from excessive to nonexistent. In a catheter that approaches the intersection of the ostium and the atrium in a "forward" direction, the disparity between the generally motionless (or out of synch) catheter and the heart makes it difficult to maintain stable contact between the catheter tip and the intersection of the flat and cavernous regions in a beating moving heart. An unsupported and thus unsynchronized catheter used in these regions may be inadvertently advanced into the pulmonary vein or venous antrum. Also, the nonuniform contours at the intersection of the pulmonary vein or venous antrum and surrounding tissue can make it difficult to contact recessed areas without excess pressure on the protruding areas increasing the risk of perforation. In addition, the catheter position is maintained only by contact between the tip and the nonuniform contours causing the catheter tip to frequently lose contact with the tissue during ablation or mapping as the heart moves independently during systole, diastole and with respiration.

Accordingly, a need still exists for a catheter capable of effectively mapping and ablating regions at or near the intersection of the left atrium and the ostium of a pulmonary vein or venous antrum, where the catheter is better configured and adapted for use in such regions so as to contact the nonuniform tissue surface without undue force and maintain stability during ablation and mapping despite the motion of beating heart in a breathing patient. A catheter of such design improves precision of mapping and/or ablation and minimize risks of damage to the tissue, including tissue perforation and inadvertent entry into the pulmonary vein or pulmonary venous antrum causing stenosis of the cavernous structure.

SUMMARY OF THE INVENTION

The present invention is directed to a catheter configured for mapping and ablation at a junction of a generally flat open region of the heart such as the left atrium and a generally cavernous region of the heart, such as a pulmonary vein or an antrum of several (more than one) pulmonary veins, referred to as a pulmonary venous antrum. In one embodiment, the catheter has an intermediate section with a pre-shaped section at its distal end, and a tip assembly adapted for mapping and/or ablation that is attached distally to the pre-shaped section by a flexible section that allows the tip assembly to be moved generally independently of the intermediate section. In one embodiment, the catheter comprises an elongated flexible tubular catheter body having proximal and distal ends. The deflectable intermediate section is mounted on the distal end of the tubular body and comprises at its distal end the pre-shaped curve whose curvature is generally opposite of the direction of deflection and generally conforms to a pulmonary vein or pulmonary venous antrum. The tip assembly which can have a generally straight configuration is attached to the end of the pre-shaped curve of the intermediate section by the flexible section which is configured with preset angles to extend the tip assembly off-axis and/or off-plane relative to the pre-shaped curve of the intermediate section. The intermediate section of the catheter is adapted to rest within the generally cavernous structure providing stability to the tip assembly. The flexible section improves the ability of the tip assembly to contact and remain in contact with surrounding tissues of variable contour without undue pressure. Moreover, the flexible tubing may be reinforced to provide the tip assembly with lateral stability. Accordingly, the catheter of the present invention has improved safety features and improved ablation and mapping capabilities.

In one embodiment, the tip assembly is configured as an ablation assembly that may be irrigated, comprising a plurality of irrigation ports in between which an ablation coil electrode is wound. A porous covering, preferably made of expanded polytetrafluoroethylene, covers the coil electrode and irrigation ports. Fluid passes through the irrigation ports to the porous covering, which then disperses the fluid around the ablation assembly. This irrigation generally enables the creation of deeper lesions.

In use, the distal end of the catheter is inserted into the heart of a patient. The pre-shaped section is deflected or otherwise positioned to sit in the generally cavernous region of the heart. The off-axis angle of the tip assembly readily allows the tip assembly to contact the surrounding tissue despite varied surface contour. As the user operates the catheter and maneuvers the tip assembly, the pre-shaped section advantageously maintains the tip assembly just outside the ostium of the cavernous region while the flexible section advantageously allows the tip assembly to flex from the preset off-axis angle as needed in order to remain in contact with the tissue. In one embodiment, as the tip assembly encounters protrusions and recesses outside the ostium of the pulmonary vein or pulmonary venous antrum, the tip assembly is jarred from its preset off axis angle but the flexible section allows the tip assembly to conform and ride along on the uneven surface without displacing the pre-shaped curve.

By adjusting the preset angles of the flexible section, the off-axis and/or off-plane angles of the tip assembly relative to the pre shaped curve can be adapted to ablate and/or map most if not all regions around the ostium of the pulmonary vein, pulmonary venous antrum and other generally cavernous regions of the heart with uneven tissue surface. Accordingly, generally continuous linear and/or circumferential ablation and mapping can be accomplished by respectively dragging the catheter and/or rotating the catheter control handle despite uneven tissue surface.

BRIEF DESCRIPTION OF THE DRAWINGS

These and other features and advantages of the present invention will be better understood by reference to the following detailed description when considered in conjunction with the accompanying drawings, wherein:

FIG. 2a is a side cross-sectional view of a catheter body according to the catheter of FIG. 1, including the junction between the catheter body and the intermediate section;

FIG. 2b is a side cross sectional view taken of the side opposite that of FIG. 2a of the catheter body of FIG. 2a, including the junction between the catheter body and the intermediate section;

FIG. 3a is a longitudinal cross-sectional view of the intermediate section of FIG. 3 taken along line 3a-3a;

FIG. 3b is a side cross-sectional view of the flexible section of the catheter of FIG. 1, including the junction between the flexible section and the tip assembly;

FIG. 6a is a schematic perspective view of FIG. 1, with the distal end of the intermediate section positioned within a pulmonary vein with the flexible section resting on the ostium of the pulmonary vein and the tip assembly of the catheter on the left atrium at the junction of the atria and ostium of the pulmonary vein.

DETAILED DESCRIPTION OF THE INVENTION

Figure 1:
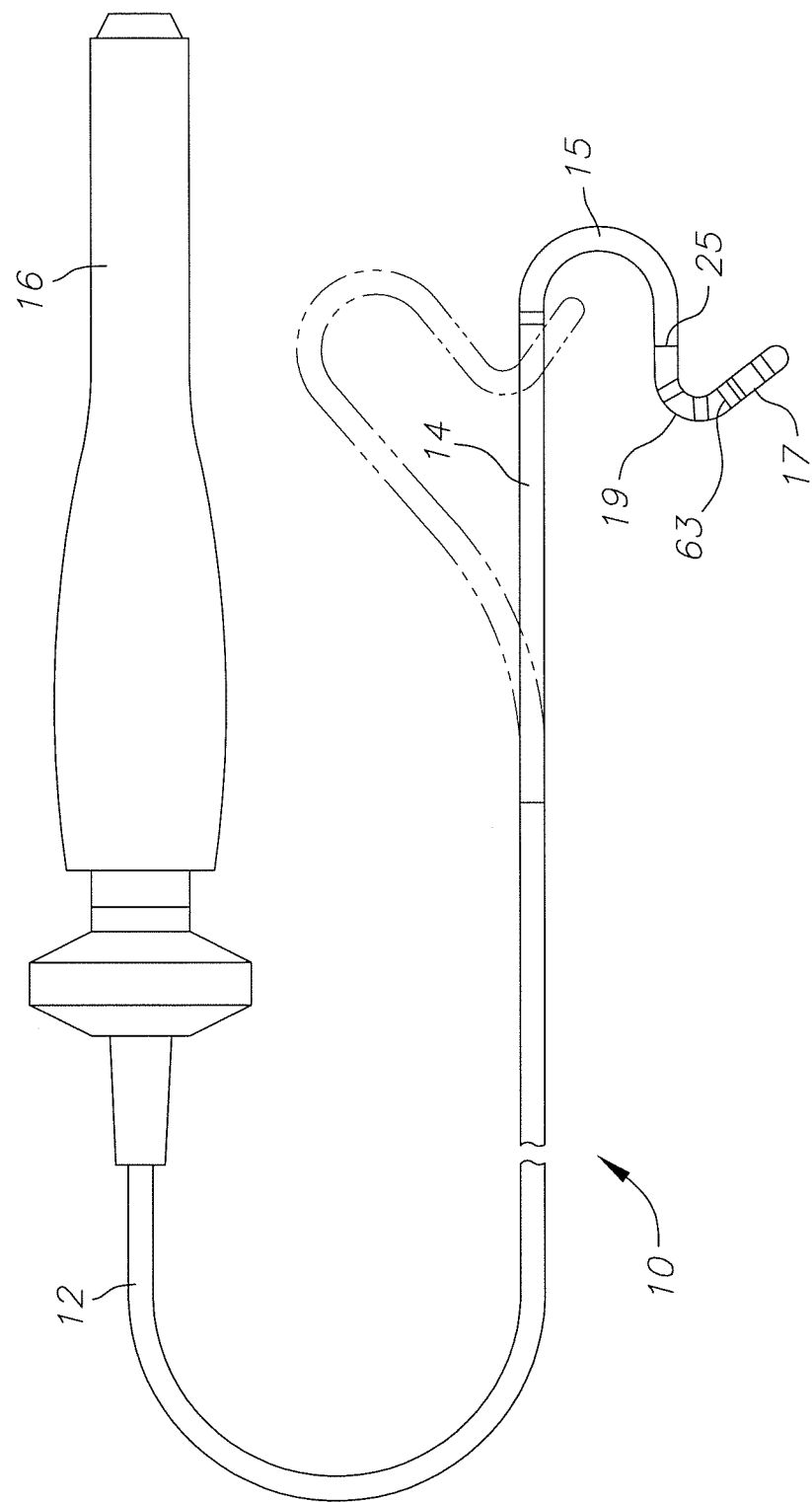
FIG. 1 is an elevated side view of one embodiment of the catheter according to the invention.

Referring to FIG. 1, the present invention provides a catheter 10 having a tip assembly 17 at its distal end. The catheter comprises an elongated catheter body 12 having proximal and distal ends, a deflectable intermediate section 14 at the distal end of the catheter body 12, and a control handle 16 at the proximal end of the catheter body. In accordance with a feature of the present invention, the tip assembly 17 extends distally from a preformed section 15 at the distal end of the intermediate section 14 and is connected thereto by a flexible section 19. In the illustrated embodiment, the tip assembly 17 is adapted for ablation although it is understood by one of ordinary skill in the art that the tip assembly may be adapted for mapping applications, as well.

Figure 1A:
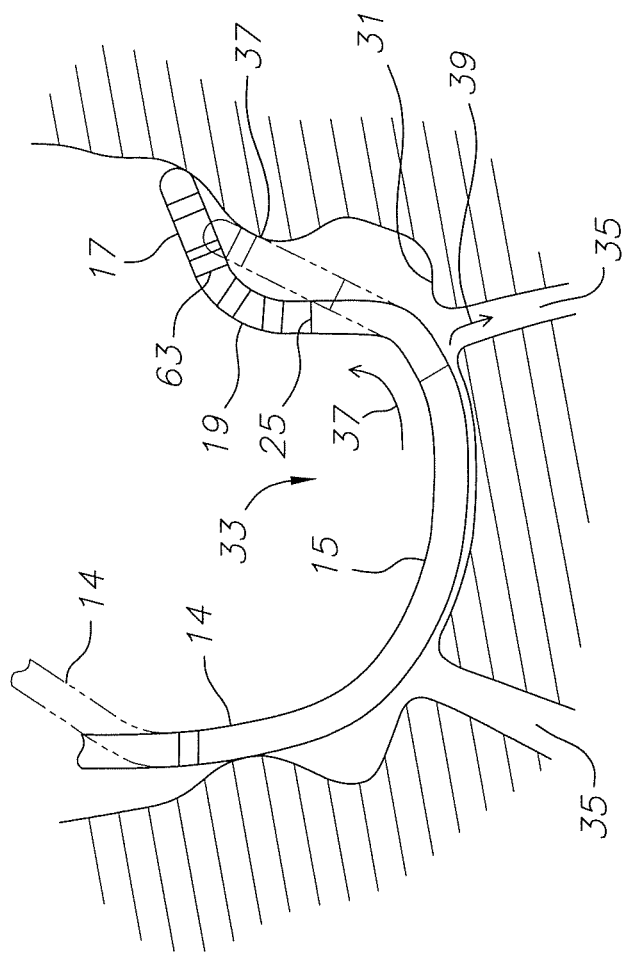
FIG. 1a is a schematic perspective view of the distal end of the intermediate section, the flexible section and the tip assembly of the catheter of FIG. 1 positioned within a generally cavernous region of the heart, such as the pulmonary venous antrum.

In the embodiment of FIG. 1A, the preformed section 15 is a curve which enables the catheter distal end when advanced and maneuvered in a generally cavernous region or structure such as a PV ostium 31 or antrum 33 to sit in and be cradled by the region with the tip assembly outside the cavernous structure. Where the cavernous structure is a pulmonary vein 35 or pulmonary venous antrum 33 the tip assembly will rest generally outside the ostium at a juncture of the pulmonary vein or venous antrum and the left atrium. The curve 15 minimizes inadvertent entry of the tip assembly into a pulmonary vein 35 or pulmonary venous antrum 33 especially where the curvature of the curve 15 is generally opposite the deflection of the intermediate section 14 (see FIG. 1). The curve 15 can therefore sit in conformity with the generally concave configuration of the ostium or antrum to urge the distal end of the catheter out of and away from entering the pulmonary vein or pulmonary venous antrum when a user advances the catheter in those regions. Accordingly, a feature of the present invention enables a user to approach the junction of the pulmonary vein or pulmonary venous antrum and the left atrium from more a "backward" direction or deflection. With the intermediate section 14 cradled in the cavernous structure the distal section of the catheter moves with the heart during systole, diastole and respiration. The tip assembly 17 is thus stable in a position at the junction of the left atrium and the pulmonary antrum/vein. The more stable backward approach with the intermediate section cradled in the pulmonary vein or pulmonary venous antrum minimizes the risk of the tip assembly inadvertently entering the pulmonary vein or pulmonary venous antrum causing damage to the veins or ineffective ablation.

Moreover, as another feature of the present invention, the flexible section 19 has a bending modulus greater than that of the preformed section 15, as discussed in detail further below. This greater flexibility enables the tip assembly 17 to flex and adjust to the contour of the tissue surface independently of the curve 15 of the intermediate section 14. As shown in FIG. 1A, the distal end of the catheter 10 is therefore better equipped to adjust to and withstand jarring of the tip assembly 17 as it comes into contact with protrusion 37 in the tissue surface when the tip assembly 17 is dragged along it. In addition, the ablation to flex and adjust permits the tip assembly to contact tissue in recessed areas without exerting excess contact pressure in elevated areas reducing the risk of perforation To that end, as also discussed in further detail below, the flexible section 19 may be configured with an off axis angle and/or off-plane angle for use in the ostium of the pulmonary vein or ostium of the pulmonary venous antrum.

With reference to FIGS. 2a and 2b, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 is able to rotate in a corresponding manner.

The outer diameter of the catheter body 12 is not critical, but is preferably no more than about 9 french, more preferably about 7 french. Likewise, the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube 21 to provide improved torsional stability. A particularly preferred catheter 10 has an outer wall 20 with an outer diameter of from about 0.090 inches to about 0.094 inches and an inner diameter of from about 0.061 inches to about 0.065 inches.

Figure 2C:
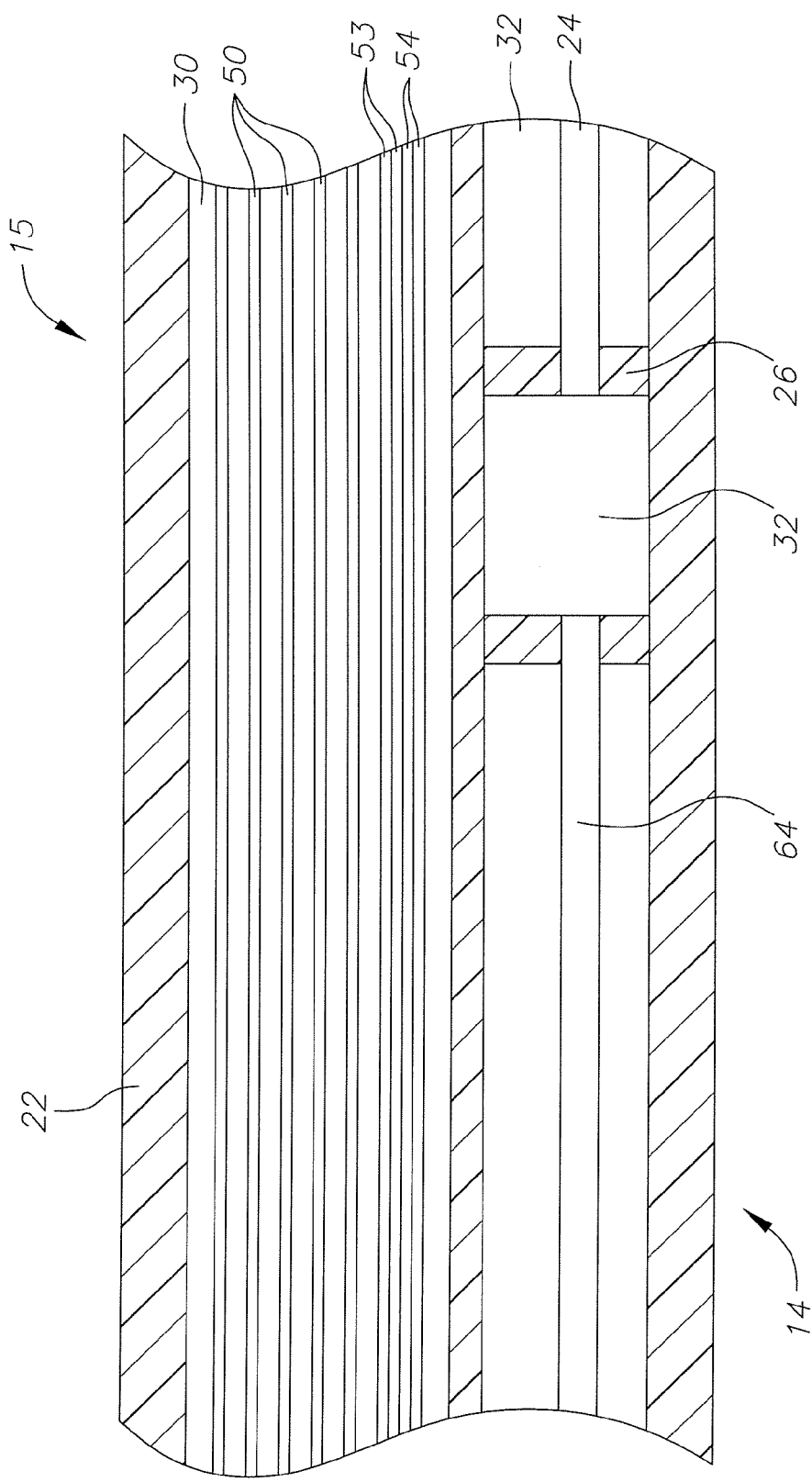
FIG. 2c is a side cross-sectional view of the intermediate section of the catheter of FIGS. 2a and 2b, including the distal end of a puller wire and the proximal end of a shape memory support member.
Figure 3:
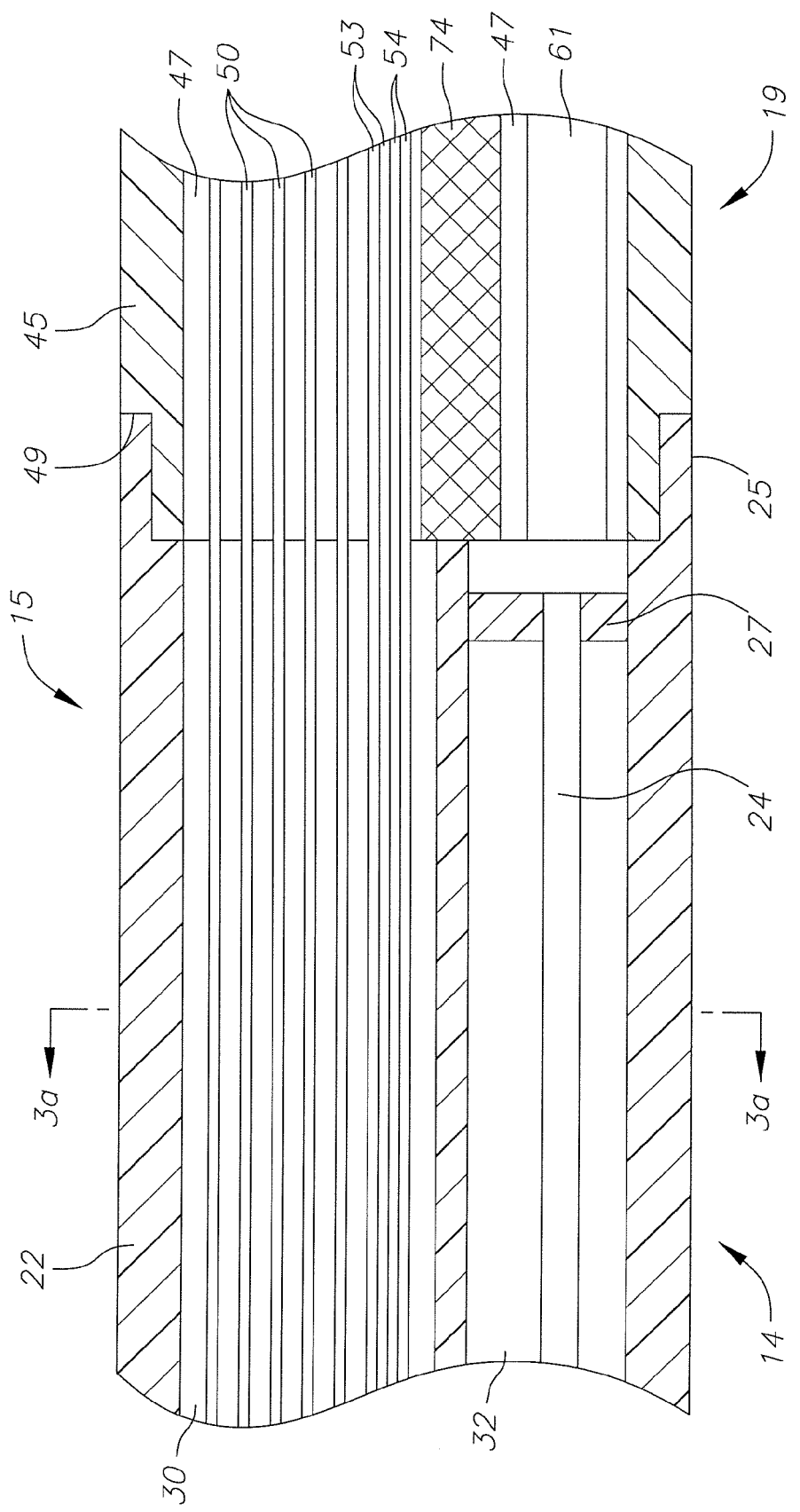
FIG. 3 is a side cross-sectional view of the intermediate section of the catheter of FIG. 1, including the junction between the intermediate section and the flexible section.
Figure 3A:
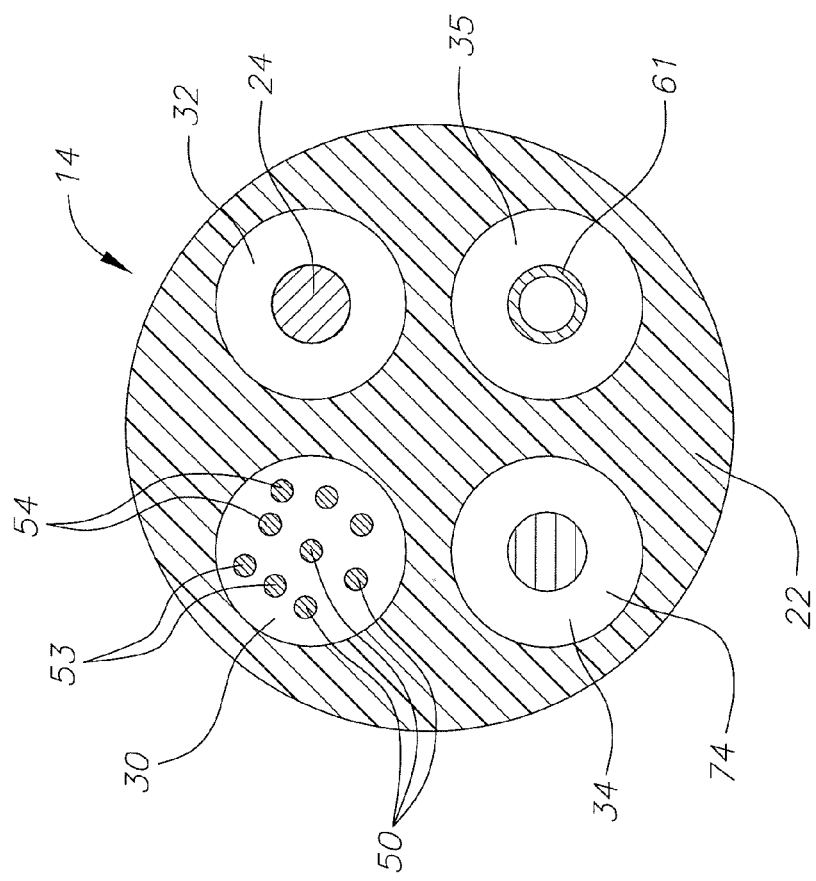

The intermediate section 14 comprises a short section of tubing 22 having multiple lumens, as shown in FIG. 3a. In one embodiment, a first lumen 30 carries one or more lead wires 50 and any other components (e.g., thermocouple wires 53 and 54 for monitoring tissue temperature) extending along the catheter (FIGS. 2a, 2c and 3). A second lumen 32 carries a puller wire 64 in the more proximal region (FIGS. 2a and 2c), and a support member 24 in the more distal region (FIGS. 2c and 3) which enables shape memory curvature of the pre-formed curve 15. As also shown in FIGS. 2b, a third lumen 34 carries an electromagnetic sensor cable 74, and a fourth lumen 35 carries an irrigation tube 61 for supplying fluid to the tip assembly 17. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The number of lumens or the size of each lumen is not critical, but is sufficient to house the lead wires, puller wire, electromagnetic sensor cable, thermal sensors and/or irrigation tube(s) depending on the embodiment.

The useful length of the catheter 10, i.e., that portion that can be inserted into the body excluding the tip assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 2a and 2b. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube 21 and the proximal end of the intermediate section. The spacer provides a transition in flexibility at the junction of the catheter body and intermediate section, which allows the junction to bend smoothly without folding or kinking. A catheter having such a spacer is described in U.S. Pat. No. 5,964,757, the entire disclosure of which is incorporated herein by reference.

Figure 6B:
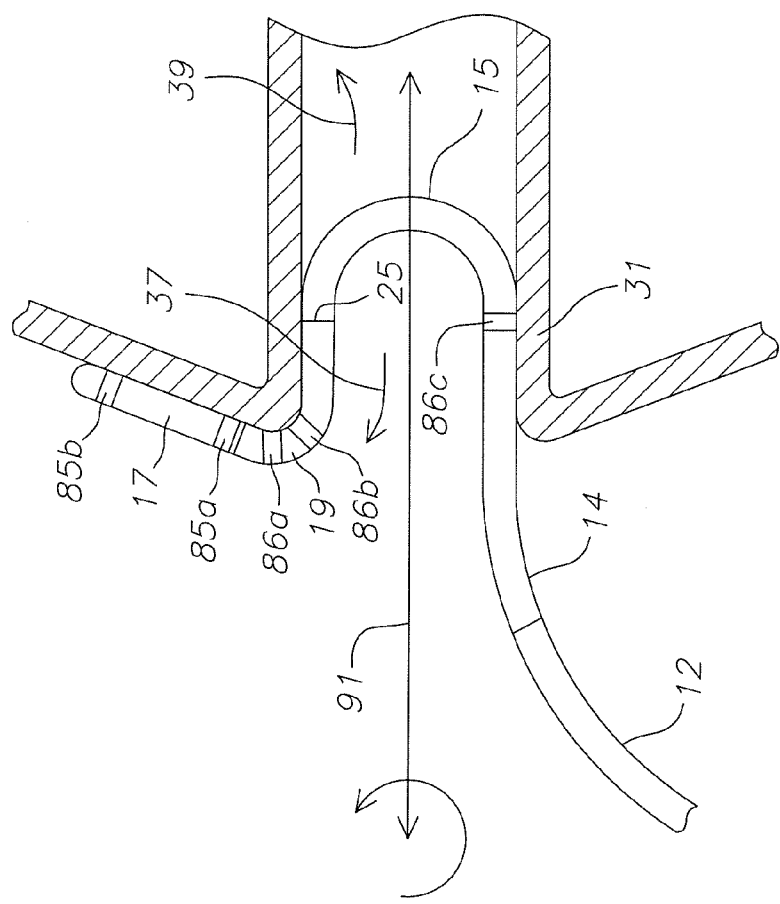
FIG. 6b is a schematic perspective view of the distal end of the intermediate section of FIG. 1 in a deflected position, positioned within a pulmonary vein. The flexible section is at the ostium and the tip assembly is on the generally flat atrium.

As shown in FIG. 2a, the puller wire 64 is provided for deflection of the intermediate section 14 (see FIGS. 1 and 6b). The puller wire 64 extends through the catheter body 12, is anchored at its proximal end to the control handle 16, and is anchored at its distal end to the intermediate section 14. The distal end of the puller wire 64 is anchored within the intermediate section 14 at about the location of the termination of the proximal end of the support member 24. The puller wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to the puller wire 64, as shown in FIG. 2a. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. The outer surface of the compression coil 66 is covered by a flexible, non-conductive sheath 68, e.g., made of polyimide tubing.

The compression coil 66 is anchored to the outer wall of the catheter body 12 by proximal glue joint 70 and at its distal end to the intermediate section 14 by distal glue joint 71. Both glue joints 70 and 71 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

Longitudinal movement of the puller wire 64 relative to the catheter body 12, which results in deflection of the intermediate section 14 (FIG. 1), is accomplished by suitable manipulation of the control handle 16. Examples of suitable control handles for use in the present invention are disclosed in U.S. Pat. Nos. Re 34,502 and 5,897,529, the entire disclosures of which are incorporated herein by reference. Deflection of the intermediate section 14 by longitudinal movement of the puller wire 64 generally results in deflection of the preformed shaped curve 15 of the intermediate section 14, as well as the entire tip assembly 17, without distortion of the curve 15. Deflection of the intermediate section 14 in this manner enables better maneuverability of the curve 15 within the heart. In the illustrated embodiment, the puller wire is configured to deflect the intermediate section 14 in a direction away from the curvature of the curve 15. As understood by one of ordinary skill in the art, the puller wire may be configured as appropriate to enable deflection of the intermediate section 14 in other directions.

Figure 4:
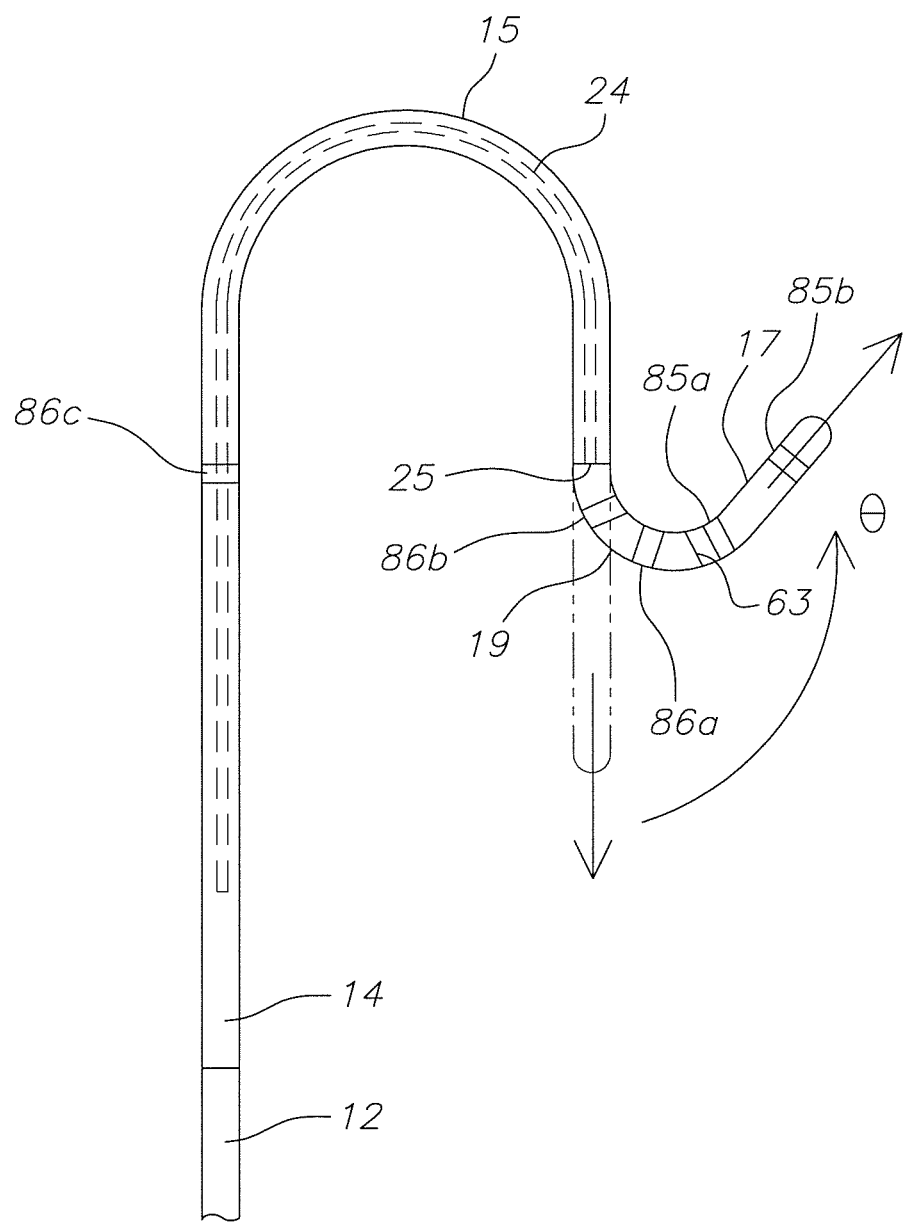
FIG. 4 is an enlarged side view of the distal end of the intermediate section, the flexible section and the tip assembly according to the embodiment of FIG. 1.
Figure 4A:
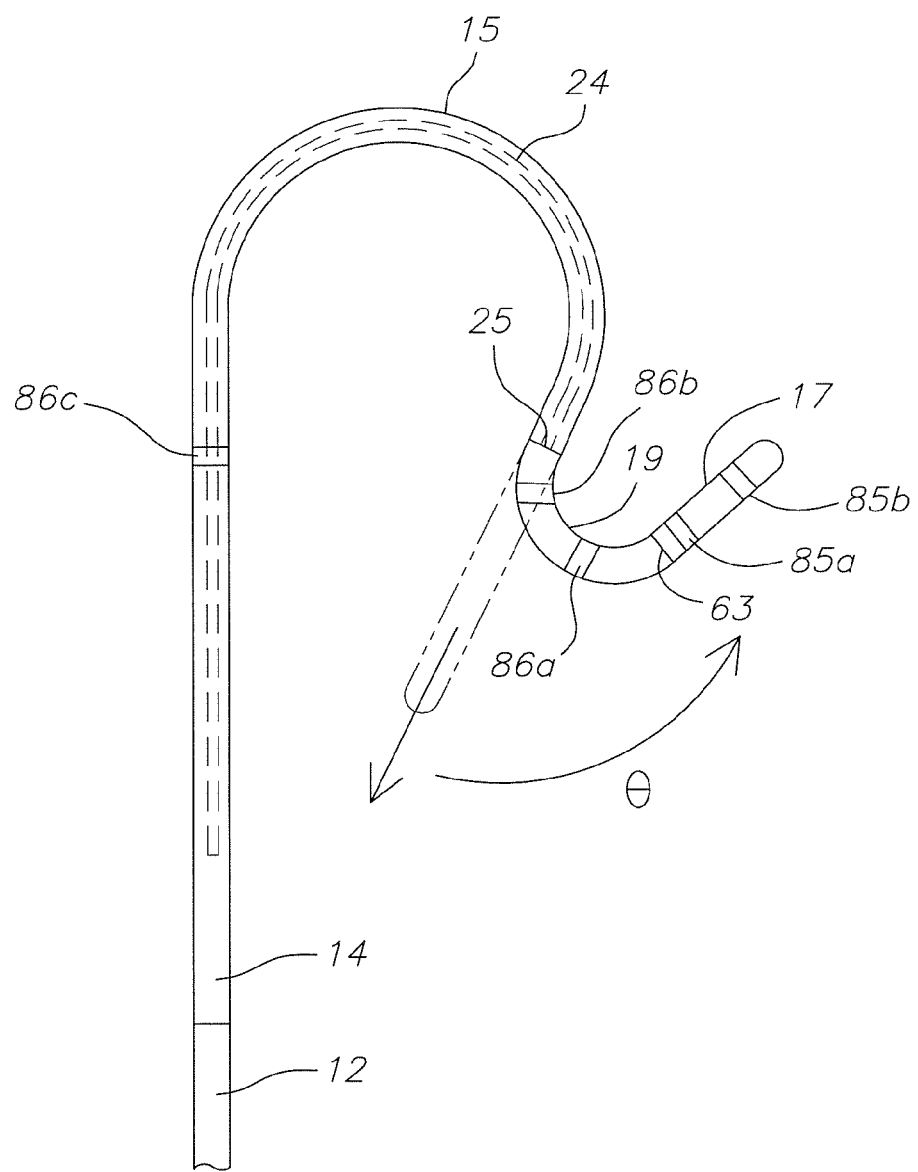
FIG. 4a is an enlarged side view of the distal end of the intermediate section, the flexible section and the tip assembly according to an alternative embodiment.

The distal portion of the intermediate section 14, containing the support member 24, terminates in the preformed curve 15, better shown in FIGS. 4 and 4A. The support member 24 (shown in broken lines) is made of a material having shape-memory, i.e., that can be straightened or bent out of its original shape upon exertion of a force and is capable of substantially returning to its original shape upon removal of the force. A particularly preferred material for the support member 24 is a nickel/titanium alloy wire or ribbon. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability. As such, the support member 24 enables the catheter to be advanced atraumatically in the patient's body in a generally straight configuration through a vein or artery and yet be able to assume its preformed shape when it reaches the heart. The support member 24 extends proximally from a junction 25 of the intermediate section 14 and the flexible section 19, through the third lumen 34 (FIG. 2c) of the intermediate section 14 and terminates at about a third of the length of the intermediate section 14, so as not to adversely affect the ability of the intermediate section 14 to deflect. The distal and proximal ends of the support member 24 are anchored to the lumen 32 by any suitable means, for example, adhesives forming glue joints 26 (FIGS. 2c) and 27 (FIG. 3).

The preformed curve 15 is prepared by placing the support member 24 in a delrin mold and heating the support member in the mold at about 550° C. for about 15 minutes. The tubing 22 of the intermediate section 14 is also preformed to include the curve 15 by placing the tubing 22 in a delrin mold and heating the mold at about 100° C. for about 30 minutes. The length of the curve 15 of the intermediate section 14 can vary as desired, but is preferably no longer than about 33 mm, preferably about 10 mm.

The curvature of the preshaped section 15 enables it to fit and sit within a generally cavernous structure such as a pulmonary vein (FIGS. 6a and 6b) or a pulmonary venous antrum (FIG. 1A) for pulmonary vein isolation. In the illustrated embodiments, the pre-shaped curve 15 is generally circular to conform to the overall shape and cavity of the pulmonary vein and pulmonary venous antrum. However, recognizing that pulmonary veins and pulmonary venous antrums can come in different shapes and sizes, the curve 15 may have a general diameter ranging between about 0.5 cm and 6.0 cm, more preferably between about 1.0 cm and 3.0 cm, and a curvature ranging between about 110 degrees and 270 degrees (a more closed or "hook" shape as shown in FIG. 4A). The preferred shape is a generally U shape as shown in FIG. 4 with a curvature of about 180 degrees. It is understood that the curve 15 may assume a variety of sizes and shapes as desirable or appropriate for the intended region of ablation or mapping.

By conforming to the shape of the region, the curve 15 sits securely in the region and transmits the motion of the heart during systole, diastole and respiration to the entire catheter. The tip of the catheter is thus both stable and moves in synchrony with the heart. This allows the distal end of the catheter to be maneuvered with minimal risk of the tip assembly inadvertently entering a tubular region in communication with the region. In the illustrated embodiment, the curve 15 tends to guide the distal end of the catheter out of the vein or venous antrum when the catheter body is advanced at or near the treatment site. As shown in FIGS. 1A, 6 and 6a, as the catheter is advanced in the vein or venous antrum, the curve 15 being in conformity with the shape of the vein or venous antrum predisposes the distal end of the catheter to turn back or curl on itself (along direction 37) and out of the vein 35 or venous antrum 33, as opposed to advancing in an opposite direction from the curvature of the curve 15 (along direction 39) which may lead the tip assembly 17 downwardly into a pulmonary vein 35 or pulmonary venous antrum 33.

In accordance with another feature of the present invention, the tip assembly 17 is attached to the distal end of the curve 15 of the intermediate section 14 by the flexible section 19. As shown in FIGS. 4 and 4A, the flexible section 19 supports the tip assembly 17 at a preset off-axis from the distal end of the curve 15. Using an angle $\theta$ to define the off-axis angle, the angle $\theta$ may range between about 10 degrees to about 180 degrees, preferably between about 70 degrees to 150 degrees, and more preferably about 120 degrees. In the embodiment of FIG. 4, the angle $\theta$ is about 120 degrees and in the embodiment of FIG. 4A, the angle $\theta$ is about 160 degrees. The angle $\theta$ generally allows the tip assembly to contact the surrounding tissue. The flexible section allows the angle $\theta$ to be varied from the initially set off axis angle to zero degrees with minimal force applied to the tip assembly through contact with the tissue.

To enable the tip assembly 17 to remain in or return to contact with the tissue outside the ostium of the pulmonary vein or the pulmonary venous antrum while the distal end of the catheter is advanced, withdrawn or otherwise maneuvered in the ostium or antrum, the flexible section 19 is constructed with shape memory and/or sufficient flexibility and elasticity so that the tip assembly 17 can temporarily assume a different (greater or lesser) angle $\theta$ as needed for the tip assembly to pivot at its proximal end. The flexible section 19 can be sufficiently soft to allow the tip assembly 17 to be displaced from its preset off-axis angle $\theta$ to an on-axis angle where $\theta$ is about zero, and sufficiently elastic to return (or at least bias the return of) the tip assembly 17 to its preset off-axis angle $\theta$ thereafter, whether the displacement was caused by a formation 37 in the surrounding tissue, the tip assembly being caught or buried in the surrounding tissue, or a "steam pop" where a build up of pressure dislodges the tip assembly from contact with the surrounding tissue. To that end, the flexible section 19 has a relatively high flexural modulus measuring on a Durometer scale no greater than about 25 D to 35 D and/or no greater than about ½ to ¼ of the Durometer measurement of the curve 15. As shown in FIG. 1A, the flexible section 19 acts as a "shock absorber" when the tip assembly is jarred or otherwise displaced from its preset position. The flexible section 19 enables the tip assembly 17 to pivot to away from the protrusion 37 independently of the intermediate section 14 so that the tip assembly can remain in contact with the tissue. As the catheter 10 is advanced, withdrawn or otherwise maneuvered around the treatment site, the tip assembly 17 moves between a resting position A (solid lines) and a displaced position B (broken lines) without significantly displacing the curve 15 of the intermediate section 14 or changing its curvature. In one embodiment, the tip assembly 17 can be displaced from its preset off-axis angle (position A) under a force or weight of merely about 0.25 to about 2.0 oz, and more preferably about 1.0 ounce. As such, the flexible section 19 provides sufficient flexibility to reduce the risk of injury that can result from the tip assembly 17 inadvertently perforating tissue or being buried in the tissue and overheating. As understood by one of ordinary skill in the art, the force required to displace or capable of displacing the tip assembly from the preset off axis angle depends on the point of application of the force to the tip assembly, as well as the length of the tip assembly.

Figure 3C:
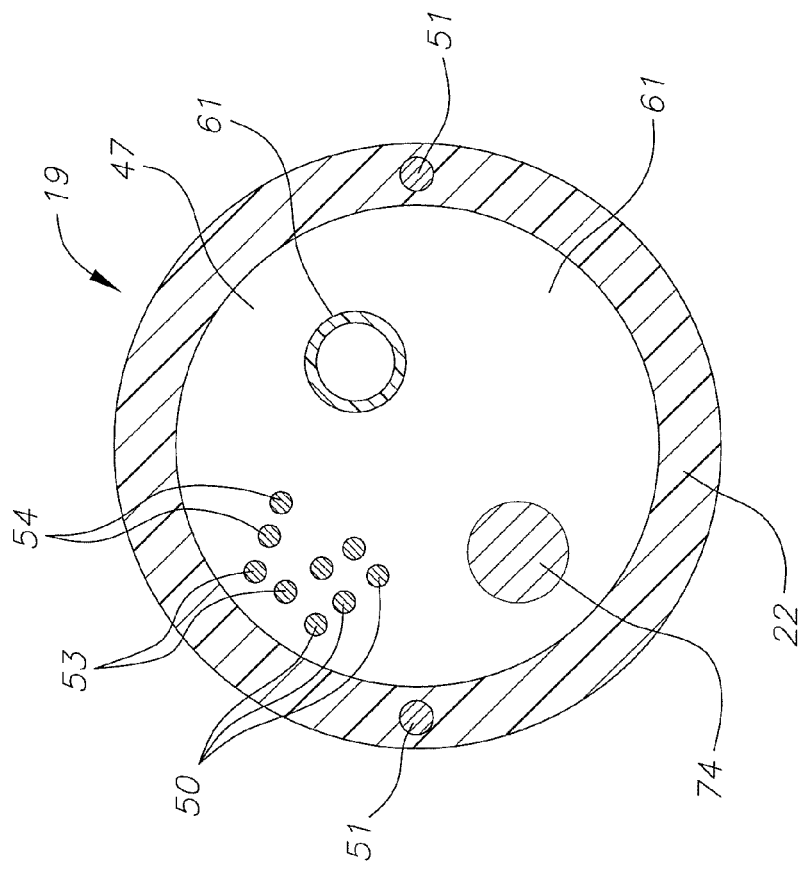
FIG. 3c is a longitudinal cross-section view of the flexible section of FIG. 3 taken along line 3d-3d.
Figure 4B:
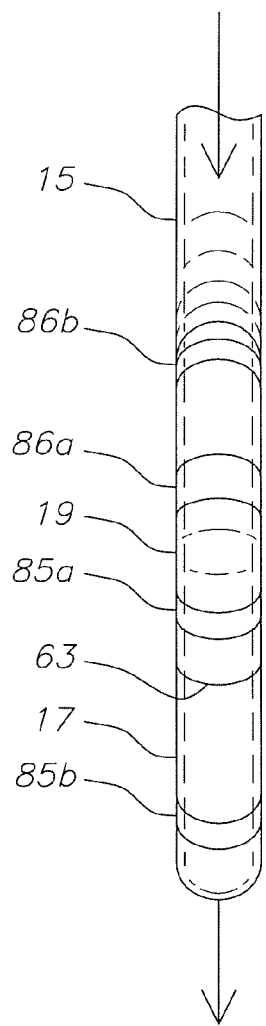
FIG. 4b is a bottom end view of the distal curve of the intermediate section, the flexible section and the tip assembly of FIG. 4, with the flexible section preset to support the tip assembly in-plain with the distal curve of the intermediate section.
Figure 4C:
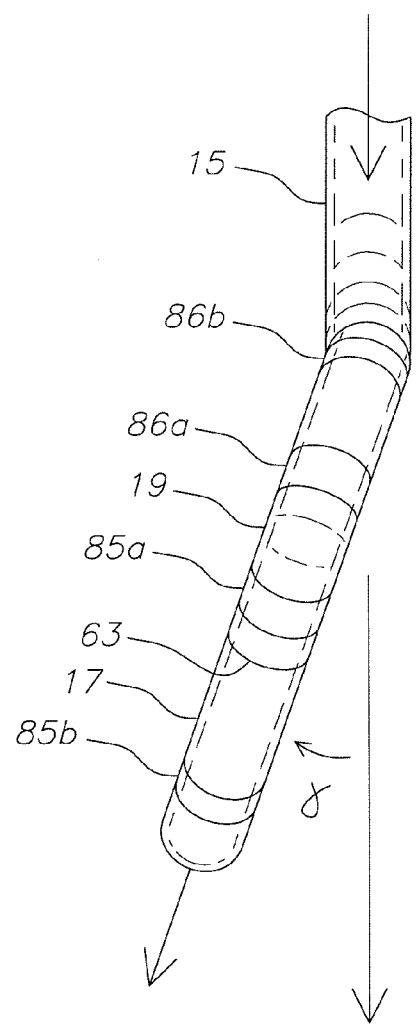
FIG. 4c is a bottom end view of the distal curve of the intermediate section, the flexible section and the tip assembly of FIG. 4b, with the flexible section preset to support the tip assembly off-plane with the distal curve of the intermediate section.

Referring to FIGS. 4b and 4c, the highly flexible section 19 may also be configured to support the tip assembly 17 off-plane from the curve 15 at a variety of radial angles. Using angle γ to define the radial angle from a plane defined by the curve 15, the angle γ may range between about 0 to 360 degrees, preferably about 20 to 90 degrees, and more preferably about 40 degrees. As understood by one of ordinary skill in the art, the angle γ can be preset to any degrees depending on the location and surrounding structures of the tissue to be ablated or mapped. In the embodiment of FIG. 4b, the angle γ is about zero degrees in that the tip assembly 17 lies in the plane of the curve 15 with the flexible section 19 extending the tip assembly in a direction or curvature generally opposite to the curvature of the curve 15. In the embodiment of FIG. 4C, the angle γ is about 40 degrees. Moreover, to provide lateral stability in the tip assembly 17, struts or ribbons 51 may be provided in walls of the tubing 45, as shown in FIG. 3c, or elsewhere on or in the tubing as desirable. A pair of struts 51 can be aligned along a diameter that is generally perpendicular to a plane defined by the angle γ for maximum lateral stability while minimizing interference with movement of the tip assembly between the off- and on-axis positions.

The flexible section 19 comprises a short section of tubing 45 with a central lumen 47 through which the lead wires 50, thermocouple wires 53 and 54, sensor cable 74 and irrigation tube 61 extend distally and connect to the tip assembly 17. A junction 25 of the intermediate section 14 and the flexible section 19 is shown in FIG. 3. The proximal end of the tubing 45 of the tip assembly 17 comprises an outer circumferential notch 49 that receives the inner surface of the tubing 22 of the intermediate section 14. The intermediate section 14 and the flexible section 19 are attached by glue or the like. The tubing 45 of the flexible section can be made of polyurethane, PEBAX, silicone or combinations thereof and is preformed (used generally interchangeably with "preshaped" herein) with shape memory by placing the tubing 45 in a delrin mold and heating the mold at about 100° C. for about 30 minutes. The length of the flexible section 19 can vary as desired and can range between about 0.1 cm and 2.0 cm, preferably between about 0.2 cm and 1.0 cm, and more preferably about 5.0 cm.

In illustrated embodiment, the tip assembly 17 comprises a short section of tubing 61 (FIGS. 3b, 5a and 5b) comprising four lumens 30a, 32a, 34a and 35a, generally corresponding to and aligned with the four lumens 30, 32, 34 and 35 respectively, of the intermediate section 14. The length of the tip assembly 17 can vary as desired, but preferably ranges between about 8 mm to about 15 mm, and more preferably is about 10 mm. A junction 63 of the flexible section 19 and the tip assembly 17 is shown in FIG. 3B. The proximal end of the tubing 61 of the tip assembly 17 comprises an outer circumferential notch 65 that receives the inner surface of the tubing 45 of the flexible section 19. The flexible section 19 and tip assembly 17 are attached by glue or the like.

Figure 5A:
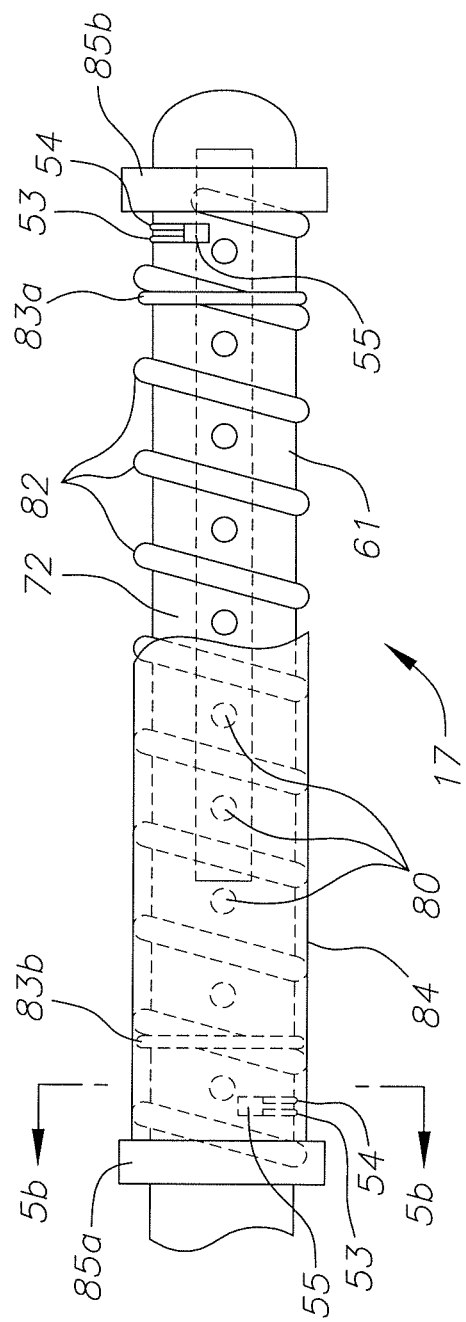
FIG. 5a is a close-up side view of an embodiment of an irrigated ablation assembly.

FIG. 5a illustrates an embodiment of the tip assembly 17 configured as an ablation assembly. A coil electrode 82 is coiled around the length of the ablation assembly 17. The longitudinal span of the coil electrode 82 may be made of any suitable metal, preferably platinum/iridium and ranges in length from about 6 to about 10 mm, preferably about 8 mm to generally match the length of the ablation assembly 17.

Figure 5B:
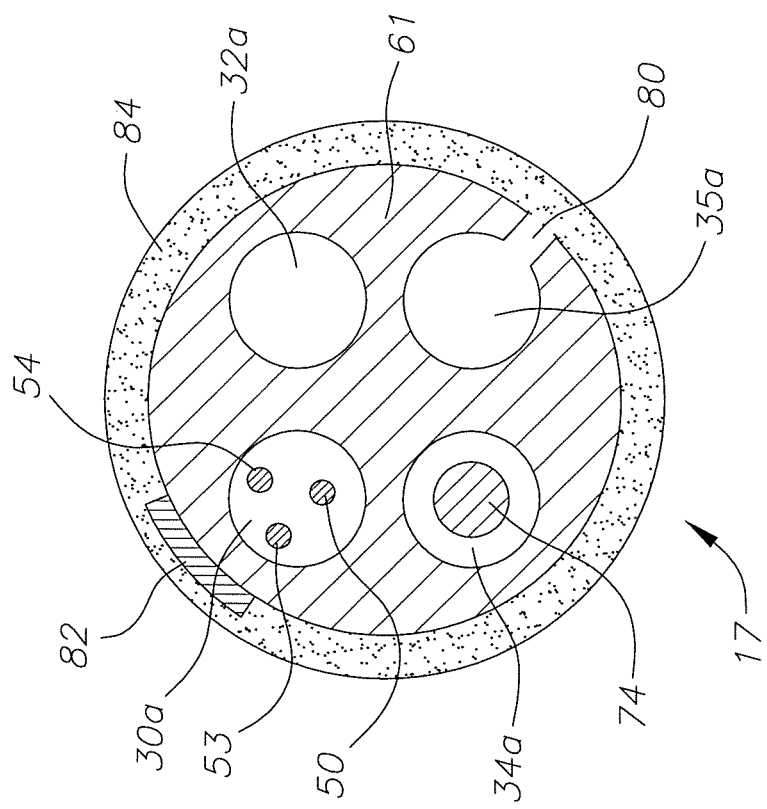
FIG. 5b is a close-up longitudinal cross-sectional view of the ablation assembly depicted in FIG. 5a taken along line 5b-5b.

In the disclosed embodiment, the ablation assembly 17 is irrigated and comprises a plurality of irrigation ports 80 disposed along most of the length of the ablation assembly 17 through which fluid can pass to the outer surface of the ablation assembly to cool the ablation site. In the illustrated embodiment, the coil and the irrigation ports 80 are arranged so that an irrigation port lies between each wind of the coil electrode 82. The irrigation ports may comprise round holes formed on the surface of the tubing 61 on the side of the ablation assembly 17 in communication with the fourth lumen 35a which is supplied fluid by the irrigation tube 61 whose distal end is slightly proximal of the most proximal irrigation port. Any number of irrigation ports 80 may be used. In the illustrated embodiment, the tubing 61 of the ablation assembly 17 is configured with about 10 irrigation ports 80. The circumference of each round hole can measure about $20/1000$ inch. As shown in FIGS. 5a and 5b, a porous protective covering 84, of, for example, expanded polytetrafluoroethylene (EPTFE), is disposed over the tubing 61 in surrounding relation to and covering the coil electrode 82 and irrigation ports 80

A tip electrode lead wire 50 (FIG. 5b) connects the coil electrode 82 to a suitable source of ablation energy (not shown), preferably radio frequency (RF) energy. The distal end of the lead wire 50 is attached to the proximal end of the coil electrode 82. The proximal end of the lead wire 50 is electrically connected to the source of ablation energy as is known in the art. The lead wire 50 extends through the first lumen 30a of the ablation assembly 17, the central lumen 47 of the flexible section 19, the first lumen 30 of the intermediate section 14, the central lumen 18 of the catheter body 12, and the control handle 16, and terminates at its proximal end in a connector (not shown).

As shown in FIG. 5a, if desired, mapping and/or ablation ring electrodes 83a and 83b may be mounted on the ablation assembly 17. The ring electrodes 83a and 83b can be mounted over the coil electrode 82 and underneath the porous covering 84. In the illustrated embodiment, the first ring electrode 83a is positioned in between the two distal most irrigation ports 80. The second ring electrode 83b is positioned in between the two proximal most irrigation ports 80. The ring electrodes 83a and 83b are mounted to the coil electrode 82 by any suitable means, for example by welding, soldering or the like. As such, the ring electrodes 83a and 83b are electrically connected to the coil electrode 82 and its associated lead wire for ablation purposes. The ring electrodes 83a and 83b serve in part to hold the coil electrode 82 in place on the tubing 61 of the ablation assembly. The ring electrodes 83*a* and 83*b* also serve to flatten the coil electrode 82 on the surface of the tubing 61, thereby preventing any rough edges of the coil electrode 82 from cutting into the porous covering 84.

Any conventional temperature sensors, e.g. thermocouples or thermistors, may be used. In the embodiment shown in FIGS. 2*a*, 3 and 5*a*, the temperature sensors comprise two thermocouples formed by two enameled wire pairs. One wire of each wire pair is a copper wire 53, e.g., a number "40" copper wire. The other wire of each wire pair is a constantan wire 54. The wires 53 and 54 of each wire pair are electrically isolated from each other except at their distal ends where they are twisted together, covered with a short piece of plastic tubing 55 (FIG. 5*a*), e.g., polyimide, and covered with epoxy. The wires 53 and 54 of each wire pair extend out a hole in the side wall of the tubing 61 and are anchored to the outer surface of tubing 61. The hole in the side wall of the distal region is sealed by a plug. Any suitable seal may be used, for example glue or the like. Each plastic tubing 55 is mounted on the outer surface of the tubing 61 by polyurethane glue or the like. One of the two thermocouples is anchored immediately distal the distal most irrigation port 80, as shown in FIG. 5*a*. The second of the two thermocouples is anchored immediately proximal the proximal most irrigation port 80. The wires 53 and 54 extend through the first lumen 30 in the ablation assembly 17 and intermediate section 14, through the central lumen 18 of the catheter body 12 and out through the control handle 16 to a connector (not shown) connectable to a temperature monitor (not shown).

If desired, one or more mapping and/or ablation ring electrodes can be mounted on the tubing 45 of the flexible section 19 and tubing 61 of the ablation assembly 17, as shown in FIGS. 4 and 5*a*. These ring electrodes might be desirable, for example, for mapping the region to be ablated before ablation begins or after ablation to assure that the lesions blocked the electrical activity as desired. A ring electrode 85*a* can be mounted on the proximal end of the tubing 61 of the ablation assembly 17 over the porous covering 84 so that the proximal end of the porous covering 84 can be tucked underneath the ring electrode 85*a* to lock the proximal position of the porous covering 84. Also, a second ring electrode 85*b* can be mounted on the distal end of the tubing 61 so that the distal end of the porous covering 84 can be tucked underneath the ring electrode 85*b* to lock the distal position of the porous covering 84.

In other embodiment, the tip assembly 17 whether adapted for mapping or ablation may be constructed with or without irrigation, with or without temperature sensors, using suitable ring electrodes for sensing and/or ablation, as understood by one of ordinary skill in the art. The relationship between the tip assembly and the flexible section remains generally as described herein.

In addition, as better shown in FIGS. 4 and 4A, two additional ring electrodes 86*a* and 86*b* for mapping are mounted on the flexible section 19. The first ring electrode 86*a* is positioned approximately 5 mm proximal the proximal locking ring electrode 85*a* and is used to confirm the position of the ablation assembly in the vein or venous antrum. The second ring electrode 86*b* is positioned approximately 2.5 mm proximal the first ring electrode 86*a* and is also used to confirm the position of the ablation assembly in the vein or venous antrum. If desired, an additional ring electrode 86*c* can be mounted on the intermediate section 14 proximal the curve 15, and distal the junction of the intermediate section 14 and catheter body 12. This additional mapping ring electrode 86*c* may be used to assure that the curve 15 of the intermediate section 14 is positioned in the desired location generally within the vein or venous antrum. As understood by one of ordinary skill in the art, the mapping electrodes may be mounted at different locations on the ablation assembly 17, flexible section 19 and/or intermediate section 14 as desired.

In FIG. 3, each ring electrode 85*a*, 85*b*, 86*a*, 86*b* and 86*c* is connected to a corresponding lead wire 50. The distal end of each lead wire 50 is attached to the corresponding ring electrode. The proximal end of each lead wire 50 is electrically connected to a suitable monitoring device for monitoring electrical activity. Each lead wire 50 extends through the first lumen 30*a* of the ablation assembly 17, the central lumen 47 of the tubing 45, the first lumen 30 of the intermediate section 14, the central lumen 18 of the catheter body 12, and the control handle 16, and terminates at its proximal end in a connector (not shown).

As shown in FIG. 2*a*, the portion of each lead wire 50 extending through the control handle 16, the central lumen 18 of the catheter body 12, and at least the proximal section of the intermediate section 14 is enclosed within a protective sheath 62 to prevent contact with other lead wires or other components of the catheter. The protective sheath 62 can be made of any suitable material, preferably polyimide. The protective sheath 62 is anchored at its distal end to the proximal end of the intermediate section 14 by gluing it in the first lumen 30 with polyurethane glue or the like. As would be recognized by one skilled in the art, the protective sheath 62 can be eliminated if desired.

As shown in FIG. 5*a*, an electromagnetic navigation sensor 72 may be contained within the ablation assembly 17. The electromagnetic sensor 72 is preferably situated at the distal tip of the ablation assembly 17 and is approximately 5 mm long. The electromagnetic sensor 72 is positioned in the third lumen 34*a* of the ablation assembly 17. The electromagnetic sensor 72 is mounted to the tubing 61 of the ablation assembly 17 by any suitable means, e.g. by polyurethane glue or the like.

The electromagnetic sensor 72 is connected to an electromagnetic sensor cable 74, which extends through the third lumen 34*a* in the ablation assembly 17, the central lumen 47 of the flexible section 19, the third lumen 34 of the intermediate section 14, through the catheter body 12, and out through the control handle 16. The electromagnetic sensor cable 74 comprises multiple wires encased within a plastic covered sheath. In the control handle 16, the sensor cable 74 is connected to a circuit board (not shown). The circuit board amplifies the signal received from the electromagnetic sensor 72 and transmits it to a computer in a form understandable by the computer. Because the catheter is designed for a single use only, the circuit board may contain an EPROM chip which shuts down the circuit board approximately 24 hours after the catheter has been used. This prevents the catheter, or at least the electromagnetic sensor from being used twice.

Suitable electromagnetic sensors for use with the present invention are described, for example, in U.S. Pat. Nos. 5,558,091, 5,443,489, 5,480,422, 5,546,951, and 5,391,199, the disclosures of which are incorporated herein by reference. A preferred electromagnetic sensor 72 has a length of from about 6 mm to about 7 mm, preferably about 5 mm, and a diameter of about 1.3 mm.

In FIG. 3*a*, the irrigation tube 61 may be made of any suitable material, and is preferably made of polyimide tubing. A preferred irrigation tube has an outer diameter of from about 0.032 inch to about 0.036 inch, and an inner diameter of from about 0.028 inch to about 0.032 inch. The irrigation tube 61 extends through the central lumen 18 of the catheter body 12 (FIG. 2*b*), the fourth lumen 35 of the intermediate section 14, the central lumen 47 of the flexible section 19, and the fourth lumen 35a of the ablation assembly 17 (FIG. 3a), and terminates slight proximal of the most proximal irrigation port 80 in the ablation assembly 17. The proximal end of the irrigation tube 61 extends through the control handle 16 and terminates in a luer hub or the like (not shown). Fluid is introduced into the irrigation tube 61 through the luer hub. The fluid, e.g. saline, is then introduced to the fourth lumen 35a of the ablation assembly 17 by the irrigation tube 61 and passes to the outer surface of the tubing 61 through the irrigation ports 80 (FIG. 5a). The fluid is then dispersed over generally the entire surface of the ablation assembly 17 by the porous covering 84. This irrigation enables creation of deeper lesions.

In use, the catheter 10 is inserted into the patient through a suitable guiding sheath whose distal end is positioned at a desired mapping or ablating location. An example of a suitable guiding sheath for use in connection with the present invention is the Preface™ Braided Guiding Sheath, commercially available from Biosense Webster, Inc. (Diamond Bar, Calif.). The distal end of the sheath is guided into one of the atria. A catheter in accordance with the present invention is fed through the guiding sheath until its distal end extends out of the distal end of the guiding sheath. As the catheter 10 is fed through the guiding sheath, the tip assembly 17, the flexible section 19 and the intermediate section 14 are generally straightened to fit through the sheath. Once the distal end of the catheter is positioned at the desired mapping or ablating location, the guiding sheath is pulled proximally, allowing the deflectable intermediate section 14, the flexible section 19 and the tip assembly 17 to extend outside the sheath, and return to their original preformed shapes with the tip assembly 17 extending from the curve 15 at a predetermined off-axis angle θ and/or off-plane angle γ.

The curve 15 of the intermediate section 14 is then deflected or otherwise maneuvered to sit in the antrum (FIG. 1A) or vein (FIGS. 6a and 6b) which can be approached from a more "backward" direction being that the curvature of the curve 15 is generally opposite to the direction of deflection. The user can then position the catheter 10 with minimal risk of the tip assembly 17 entering a pulmonary vein.

The curve 15 of the intermediate section 14 stabilizes the tip assembly 17 in the region and the tip assembly 17 makes contact with tissue in the region by means of the preset off-axis angle provided by the flexible section 19. To create generally continuous lesions during ablation, the catheter is advanced, withdrawn and/or rotated to drag the tip assembly 17 along the tissue surface. As the ablation assembly encounters uneven formation such as a projection or recess in the tissue surface, the flexible section 19 flexes as the ablation assembly pivots from the preset off-axis angle to absorb the movement without displacing the curve 15 of the intermediate section 14 in the pulmonary venous antrum or pulmonary vein. Whether the tip assembly 17 is maneuvered linearly or rotated via the control handle 16 and/or the catheter body 12, the tip assembly 17 maintains continuous contact with the tissue for improved mapping and/or creation of lesions. In the embodiment of the catheter for mapping applications, similar manipulations of the catheter and the control handle enable the mapping electrodes 85a, 85b, 86a, 86b and 86c to map in a linear or circumferential pattern.

The preceding description has been presented with reference to presently preferred embodiments of the invention. Workers skilled in the art and technology to which this invention pertains will appreciate that the Figures are not necessarily to scale and alterations and changes in the described structure may be practiced without meaningfully departing from the principal spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A catheter comprising:
    an elongated flexible tubular catheter body having proximal and distal ends;
    an intermediate section attached to the distal end of the catheter body, a distal end of the intermediate section having a preformed curve, wherein the preformed curve of the intermediate section is adapted to sit in a generally cavernous region of or near the heart;
    a tip assembly comprising at least one of an ablation electrode or a mapping electrode; and
    a flexible section connecting the tip assembly to the preformed curve at a preset off-axis angle, the flexible section having a bending modulus greater than a bending modulus of the preformed curve of the intermediate section so that the flexible section can permit displacement of the tip assembly from the preset off-axis angle without displacement of the preformed curve in the generally, cavernous region.

2. The catheter of claim 1, wherein the flexible section connects the tip assembly to the preformed curve at a preset off-plane angle.

3. The catheter of claim 2, wherein the flexible section comprises at least one lateral support structure to minimize movement of the tip assembly from the preset off-plane angle.

4. The catheter of claim 1, wherein the intermediate section is more flexible than the catheter body.

5. The catheter of claim 1, wherein the off-axis angle ranges between 2 and 360 degrees.

6. The catheter of claim 1, wherein the displacement of the tip assembly is between the preset off-axis angle and an on-axis position.

7. A catheter of claim 1, wherein the preformed curve is substantially U shaped or substantially hook shaped.

8. A catheter of claim 1, wherein the preformed curve is configured to generally conform to a pulmonary vein or a pulmonary venous antrum.

9. A catheter of claim 1, wherein contact between the preformed curve and the generally cavernous region synchronizes a distal portion of the catheter to heart motion during systole, diastole or respiration.

10. A catheter of claim 1, wherein contact between the preformed curve and the generally cavernous region stabilizes a position of the tip assembly.

11. A method for ablating tissue at an intersection of a generally flat region and an ostium of a generally cavernous region at or near the heart, the method comprising:
    inserting into the heart a distal end of a catheter according to claim 1, wherein the tip assembly comprises the ablation electrode;
    deflecting the preformed curve to generally sit in the generally cavernous region;
    applying energy to the tip assembly while moving the tip assembly along a surface at said intersection wherein the tip assembly maintains contact with the surface to form a generally continuous lesion despite variable contour of the generally flat region.

12. A method of claim 11, wherein the tip assembly is dragged along the surface in a generally linear direction.

13. A method of claim 11, wherein the tip assembly is rotated about its axis by rotating a control handle of the catheter to form a circumferential lesion at or near said intersection.

14. A method for mapping tissue at an intersection of a generally flat region and an ostium of a generally cavernous region at or near the heart, the method comprising:
   inserting into the heart a distal end of a catheter according to claim 1, wherein the tip assembly comprises the mapping electrode;
   deflecting the preformed curve to generally sit in the generally cavernous region;
   recording electrograms from the tip assembly while moving the tip assembly along a surface at said intersection wherein the tip assembly maintains contact with the surface despite variable contour of the generally flat region.

15. A method of claim 14, wherein the tip assembly is dragged along the surface in a generally linear direction.

16. A method of claim 14, wherein the tip assembly is rotated about its axis by rotating a control handle of the catheter at or near said intersection.

17. A catheter comprising:
   an elongated flexible tubular catheter body having proximal and distal ends;
   an intermediate section attached to the distal end of the catheter body, a distal end of the intermediate section having a preformed curve, wherein the preformed curve of the intermediate section is adapted to sit in a generally cavernous region of or near the heart;
   an ablation assembly; and
   a flexible section connecting the ablation assembly to the preformed curve at a preset off-axis angle, the flexible section having a bending modulus greater than a bending modulus of the preformed curve of the intermediate section so that it can permit displacement of the ablation assembly from the preset off-axis angle without displacement of the preformed curve in the generally cavernous region.

18. The catheter of claim 17, wherein the ablation assembly comprises:
   a plurality of irrigation ports;
   a coil electrode; and
   a porous covering in surrounding relation to the coil electrode and irrigation ports.

19. The catheter of claim 18, further comprising:
   a proximal locking ring electrode mounted on a proximal region of the ablation assembly over the coil electrode and the porous covering; and
   a distal locking ring electrode mounted on a distal region of the ablation assembly over the coil electrode and the porous covering.

20. The catheter of claim 17, further comprising one or more ring electrodes proximal of the ablation assembly.

* * * * *